United States Patent
Almond et al.

(10) Patent No.: US 9,274,093 B2
(45) Date of Patent: Mar. 1, 2016

(54) METHOD FOR CHARACTERIZATION OF THE RATE OF MOVEMENT OF AN OXIDATION FRONT IN CEMENTITIOUS MATERIALS

(71) Applicant: Savannah River Nuclear Solutions, LLC, Aiken, SC (US)

(72) Inventors: Philip M. Almond, Martinez, GA (US); Christine A. Langton, Aiken, SC (US); David B. Stefanko, North Augusta, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 252 days.

(21) Appl. No.: 13/973,567

(22) Filed: Aug. 22, 2013

(65) Prior Publication Data
US 2015/0056709 A1  Feb. 26, 2015

(51) Int. Cl.
G01N 33/38 (2006.01)
G01N 33/20 (2006.01)
G01N 21/78 (2006.01)
G01N 31/22 (2006.01)
G01N 33/84 (2006.01)

(52) U.S. Cl.
CPC .............. G01N 33/383 (2013.01); G01N 21/78 (2013.01); G01N 31/22 (2013.01); G01N 33/20 (2013.01); G01N 33/84 (2013.01)

(58) Field of Classification Search
CPC ....... G01N 31/22; G01N 33/20; G01N 21/78; G01N 33/84
See application file for complete search history.

(56) References Cited

U.S. PATENT DOCUMENTS 6,797,171 B2   9/2004  Bartlett

FOREIGN PATENT DOCUMENTS

WO   WO 85/00044   1/1985

OTHER PUBLICATIONS

Method Evaluation and Field Sample Measurements for the Rate of Movement of the Oxidation Front in Saltstone P.M. Almond, D.I. Kaplan, C.A. Langton, D.B. Stefanko, W.A. Spencer, A. Hatfield, and Y. Arai SRNL-STI, Aug. 2012.*
Ex Situ Grouting of Pad A Nitrate Salt Tests Idaho National Laboratory, Appendix Q 2005.*
Almond, et al. "Method Evaluation and Field Sample Measurements for the Rate of Movement of the Oxidation Front in Saltstone"; Department of Energy; Aug. 2012.
Fuentes et al. "The Usefulness of UV-visible and Fluorescence Spectroscopies to Study the Chemical Nature of Humic Substances from Soils and Composts"; *Organic Geochemistry*; 37.12 (2006) pp. 1949-1959.

(Continued)

*Primary Examiner* — Krishnan S Menon
*Assistant Examiner* — Dwan A Gerido
(74) *Attorney, Agent, or Firm* — Dority & Manning, P.A.

(57) ABSTRACT

Disclosed are methods for determining the redox condition of cementitious materials. The methods are leaching methods that utilize a redox active transition metal indicator that is present in the cementitious material and exhibits variable solubility depending upon the oxidation state of the indicator. When the leaching process is carried out under anaerobic conditions, the presence or absence of the indicator in the leachate can be utilized to determine the redox condition of and location of the oxidation front in the material that has been subjected to the leaching process.

19 Claims, 5 Drawing Sheets

(56) References Cited

OTHER PUBLICATIONS

Rügge et al. "Characterization of Predominant Reductants in an Anaerobic Leachate-Contaminated Aquifer by Nitroaromatic Probe Compounds" *Environmental Science and Technology* 32.1 (1998) pp. 23-31.

Scott et al. "Landfill Management, Leachate Generation, and Leach Testing of Solid Wastes in Australia and Overseas".

Citation of Related Applications.

European Patent Appln. No. 14181844.3-1554; Extended European Search Report; dated Jan. 28, 2015.

Almond, et al. "Cementitious Barriers Parnership Effect of Oxidation on Chromium Leaching and Redox Capacity of Slag-Containing Waste Forms"; Mar. 1, 2013, URL:http//sti.srs.gov/fulltext/CBP-TR-2013-02.pdf.

European Patent Appln. No. 14181775.9-1554; Extended European Search Report dated Dec. 18, 2014.

Mary W. Barnes et al.: "Leaching of Saltstone" MRS Proceedings, vol. 44, Jan. 1, 1984 9 pages.

C.A. Langton: "Slag-Based Saltstone Formulations", MRS Proceedings, vol. 112, Jan. 1, 1987 10 pages.

Dusing, D.C., et al. "Effect of Redox Potential on Leaching from Stabilized/Solidified Waste Materials," 1992, J.Air Waste Manage. Assoc., vol. 42, pp. 56-62.

Harbour, J.R. et al. "Effects of Temperature and CSSX Organics on Saltstone Processing Properties," 2006, WSRC-TR-2006-00075, retrieved from internet: http://sti.srs.gov/fulltext/2006/TR200675.pdf.

* cited by examiner

METHOD FOR CHARACTERIZATION OF THE RATE OF MOVEMENT OF AN OXIDATION FRONT IN CEMENTITIOUS MATERIALS

STATEMENT AS TO RIGHTS TO INVENTIONS MADE UNDER FEDERALLY SPONSORED RESEARCH

This invention was made with Government support under Contract No. DE-AC09-08SR22470 awarded by the United States Department of Energy. The Government has certain rights in the invention.

BACKGROUND

Reprocessing is commonly used to recover plutonium, uranium, and other useful materials from spent nuclear fuel. The current standard method for reprocessing is the PUREX method, which is a liquid-liquid extraction method that can extract both uranium and plutonium independently of each other and from other fission products. Reprocessing methods generate liquid waste that includes both high activity waste (also referred to a high level waste), which carries many of the fission products and transuranic elements generated in the core, and low activity waste (also referred to a low level waste), which carries low activity fission products, actinides, and a plurality of different salts. The low activity waste is further treated to remove actinides and fission products to produce a decontaminated salt solution that, while exhibiting low activity levels, must be properly treated and stored to prevent release of contaminants.

Treatment of the decontaminated salt solution includes mixing it with a blend of cementitious materials to form a grout mixture. Upon curing of the grout mixture through hydration reactions a hardened monolithic cementitious waste form known as saltstone is formed. This particular treatment process is carried out at the Savannah River Site nuclear reservation in South Carolina, USA.

Some contaminants contained in such waste forms (e.g. chromium and technetium in saltstone, which are precipitated as very insoluble compounds under alkaline reducing conditions and are soluble under alkaline oxidizing conditions) exhibit a variable solubility depending upon their oxidation state, with the reduced form of the contaminants showing lower solubility. As such, reducing conditions are created in the waste form to slow and/or prevent release of contaminants. For instance, blast furnace slag is utilized in combination with a calcium silicate-based cement (e.g., Portland cement) in forming the saltstone waste form. Blast furnace slag significantly lowers the Eh, or redox potential, relative to traditional cements and thus serves to increase reducing conditions of the saltstone.

Desirably, the reduction capacity of the saltstone will persist over an extended performance period (e.g., 10,000 years) with rates of contaminant release dominated by slow changes in physiochemical properties. Even so, over time the chemical properties of the saltstone will vary as the result of exposure to air, groundwater, and other environmental factors. As a result the pH will decrease and the Eh potential will increase, as the saltstone oxidizes. For example, the rate of oxidation of the cement-slag based waste form, saltstone, has been calculated to be less than 0.5 millimeters per year based on oxygen diffusion models where diffusion rates change as a function of the square root of time. Models have considered liquid phase transport and a diffusion dominated process independent of flow through a fractured network and a shrinking core model.

Unfortunately, models are theoretical in nature, and require experimental data for verification. What are needed in the art are testing methods that can determine the rate of oxidation of cured cementitious materials. More specifically, what are needed are methods that can trace the location of an oxidation front in cementitious materials. Such methods would be of great use to verify modeling assumptions for long-term performance of materials such as saltstone, for long-term storage and disposal unit design, as well as to provide a basis for potential processing changes, such as clean cap installation criteria based on maximum allowable saltstone atmospheric exposure time.

SUMMARY

Aspects and advantages of the invention will be set forth in part in the following description, or may be obvious from the description, or may be learned through practice of the invention.

In one embodiment, disclosed is a method for determining the oxidation front in a cured cementitious material. The cementitious material includes a redox active transition metal indicator that exhibits variable solubility depending upon the oxidation state of the indicator. The method includes obtaining a sample from the cementitious material, the sample being obtained at a depth from the surface of the cementitious material. The method also includes combining the sample of the cementitious material with de-aerated water to form a mixture. The mixture includes a liquid portion, which includes the de-aerated water, and a solid portion. The mixture is maintained under anaerobic conditions for a period of time to form a leachate. Following this period of time, the method includes examining the leachate to determine the presence or quantity of the redox active transition metal indicator in the leachate. The presence or quantity of the indicator is indicative of the redox condition of the cementitious material at the sample depth. Thus, the method can be utilized to determine the location of an oxidation front within the cementitious material.

These and other features, aspects and advantages of the present disclosure will become better understood with reference to the following description and appended claims.

BRIEF DESCRIPTION OF THE FIGURES

A full and enabling disclosure of the present invention, including the best mode thereof, directed to one of ordinary skill in the art, is set forth in the specification, which makes reference to the appended figure, in which.

DETAILED DESCRIPTION

Figure 1A:
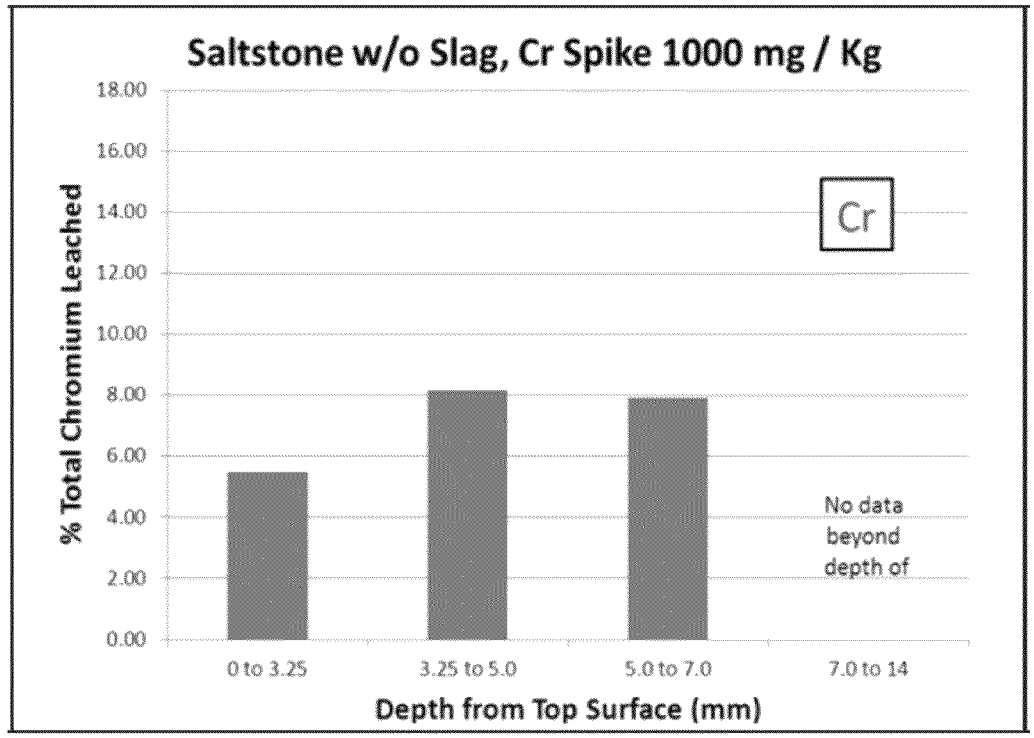
FIG. 1 illustrates the fraction of chromium (FIG. 1A) and nitrate (FIG. 1B) leached from cementitious samples that did not include ground granulated blast furnace slag.

It is to be understood by one of ordinary skill in the art that the present discussion is a description of exemplary embodiments only, and is not intended as limiting the broader aspects of the present disclosure. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

The present disclosure is generally directed to methods for determining the location of an oxidation front in cementitious materials. Disclosed methods are relatively simple, fast, and inexpensive leaching methods that can be utilized to determine the oxidation rate of a cementitious material. The disclosed methods include the incorporation of a redox active transition metal indicator in the cementitious material. The redox active transition metal indicator exhibits different solubility depending upon the oxidation state of the indicator. For example, when oxidized, the redox active transition metal indicator can be soluble and can leach from the cementitious material. However, when the cementitious material is in a reduced state, the redox active transition metal indicator can be insoluble, and little or no indicator will be detected in the leachate. The alternative situation is likewise encompassed herein, i.e., the redox active transition metal indicator can be soluble in the reduced state and can be insoluble in the oxidized state. In any case, the redox active transition metal indicator can exhibit a variation in solubility depending upon the oxidation state.

To determine the location of an oxidation front in the cementitious material, a leaching process can be carried out under anaerobic conditions with a sample of the material. For instance, a sample can be taken from a predetermined depth within the cementitious material. During the leaching process, if the redox indicator is soluble due to its oxidation state, it can leach from the cementitious sample and into the leachate as a solute. In contrast, if the indicator is insoluble due to its oxidation state, it can remain in the solid fraction of the leach mixture as the non-soluble reduced indicator. Under the anaerobic conditions of the leaching process, the redox indicator can maintain the redox condition that the indicator had while in the cementitious material prior to obtaining the sample. Thus, the redox condition of the sample can be easily determined by determination of the presence or quantity of the indicator in the leachate.

In one embodiment, the soluble indicator can have a distinct color and the presence or absence of the indicator in the leachate can be determined in a relatively simple process, for instance via visualization and/or spectroscopic examination of the anaerobic leachate.

In another embodiment the indicator can be measured using an Inductively Coupled Plasma (ICP) optical emission spectrometer or another analytical technique as known in the art.

In one embodiment, the location of an oxidation front in the cementitious material can be determined by carrying out the process multiple times, each time with a sample taken at a different depth within the cementitious material. The rate of oxidation of the cementitious material can likewise be determined by use of the method.

In another embodiment, the oxidation state of the indicator can be analyzed directly in the solid material by spectroscopy to determine the presence of the indicator (and hence the oxidation state) within the solid material without performing a leach (e.g. XAS, X-ray Absorption Spectroscopy,) as known in the art.

The redox active transition metal indicator of the blend of cementitious materials can include any transition metal that exhibits a variable solubility depending upon the oxidation state of the material. As utilized herein, the term 'blend of cementitious materials' refers to a composite that can be cured via hydration of one or more components of the blend. In general, the term does not include water that is used in forming the cured cementitious material.

In one embodiment, the redox active transition metal indicator can be chromium, which is water soluble in the fully oxidized Cr(VI) state and is insoluble in the reduced Cr(III) state. It should be understood, however, that the redox active transition metal indicator is not limited to chromium. Examples of redox active transition metal indicators can include, without limitation chromium, cobalt, copper, iron, manganese, nickel, niobium, rhenium, ruthenium, tantalum, technetium, titanium, and vanadium, which can exhibit variable solubility in aqueous media depending upon the oxidation state of the indicator.

During the reactions which form the cementitious material, the redox active transition metal indicator can be combined with the other component(s) of the blend of cementitious materials in either the oxidized or reduced state. However, it may be necessary to alter the oxidation state of the indicator during formation of the cured cementitious material. For instance, when considering the utilization of chromium as the indicator, the chromium can be combined with the other components of the blend of cementitious materials in the oxidized (soluble) state. During the hydration cure of the cementitious materials, the chromium can be reduced to the insoluble state by blast furnace slag that is included in the blend of cementitious materials. As the chromium is oxidized within the cured material, it will again become soluble and thus can be useful in determining the oxidation front in the cured cementitious material.

In general, the blend of cementitious materials will contain a relatively small amount of the redox active transition metal indicator. For example, the blend of cementitious materials can include the indicator in an amount of about 1% or less by weight, about 0.1% or less by weight, or about 0.01% or less by weight in some embodiments. For instance, the blend of cementitious materials can include the indicator in an amount of from about 0.002% by weight to about 0.01% by weight, in one embodiment. Lower concentrations may be used and are bound by the detection limits of the characterization method used for the indicator analyzed. Higher or lower concentrations can also be used if required for data interpretation. In one embodiment, the blend of cementitious materials can include from about 100 to about 10,000 mg indicator per kg of the blend of cementitious materials.

In addition to the redox active transition metal indicator, the blend of cementitious materials can include a material that can cause reduction and mitigate oxidation of the cured cementitious materials. For example, the blend of cementitious materials can include ground granulated blast furnace slag, which imparts a reducing chemistry to the material. Ground granulated blast furnace slag (also referred to throughout this disclosure as blast furnace slag) is formed from the slag by-product of cast iron production. The slag by-product is primarily a non-crystalline glassy solid that contains lime, silica and other oxides such as MgO, and $Al_2O_3$, which separate from the metal at temperatures exceeding 1900° C. The ground granulated blast furnace slag is obtained by quenching molten slag in, e.g., water or steam. When the slag is suddenly cooled in the quench, it forms a vitreous granulate. Following the quench, the glass product is then dried and ground to form the ground granulated blast furnace slag.

The specific composition of the blast furnace slag is not particularly limited and can vary depending upon the chemical composition of the slag, as is known in the art. By way of example, the quenched blast furnace slag non-crystalline solid (glass) can include from about 30% by weight to about 50% by weight calcium oxide, from about 25% by weight to about 40% by weight silicon dioxide, from about 5% by weight to about 25% by weight aluminum oxide, and from about 1% by weight to about 20% by weight magnesium oxide, and may include trace amounts (e.g., less than about 3% by weight) of iron oxide and/or sulfur trioxide.

The blast furnace slag can be any grade according to ASTM C989 as is known in the art. For example, the blast furnace slag can be Grade 80, Grade 100, or Grade 120 blast furnace slag, or mixtures thereof.

Blast furnace slag provides multiple benefits to the cementitious material. For instance, it can decrease the pH of an aqueous cementitious mixture, for instance to about pH 11, which can increase the precipitation of heavy metals in the mixture. Blast furnace slag also reduces the solubility of certain radionuclides, which can be of great benefit when utilizing the cementitious materials for long term storage of low level wastes. This can also reduce corrosion of containers that may be used to store the cured materials. The inclusion of blast furnace slag in the blend of cementitious materials can also lead to the precipitation of some cations as sulfides rather than hydroxides, which can further decrease their solubility. Moreover, blast furnace slag in the cementitious material can reduce the permeability of the cured product, which can slow degradation of the cured material and release of materials contained in the cured material.

When included, the blend of cementitious materials can include the blast furnace slag in an amount of about 20% or more by weight, for instance from about 40% by weight to 100% by weight, from about 50% by weight to about 98% by weight, or from about 55% by weight to about 95% by weight. In one embodiment, the blend of cementitious materials can include greater than about 50% by weight blast furnace slag.

The blend of cementitious materials can include other materials that can cure via hydration reaction such as, without limitation, calcium silicate based cements and natural and/or synthetic silica or alumino-silica pozzalanic materials. Calcium silicate based cements can include hydraulic cements (i.e., those that cure via hydration) such as Portland cement or Portland blended cements as are generally known in the art. A calcium silicate cement can optionally include additional materials as are known in the art such as gypsum, limestone, hydrated lime, sulfoaluminate, etc.

In one embodiment, the blend of hydraulic cementitious materials can include about 80% or less of a calcium silicate cement. For instance, the cementitious materials can include from about 2% by weight to about 50% by weight, or from about 5% by weight to about 40% by weight calcium silicate cement.

Pozzolanic materials that may be included in the blend of cementitious materials can include siliceous or siliceous and aluminous materials that when in a finely divided state and in the presence of moisture can react with calcium hydroxide to form cementitious compounds. Synthetic pozzolanic materials as may be incorporated in the blend of cementitious materials can be formed, for instance by thermal activation of kaolin-clays to obtain metakaolin, or can be obtained as waste or by-products from high-temperature processes. For instance fly ash as may be obtained as a by-product from coal-fired electricity production can be incorporated in the blend. Silica fume, a by-product of silicon smelting, is another example of a synthetic pozzolanic material as may be incorporated in the blend. Burned organic matter residues rich in silica such as rice husk ash can also be used as pozzolans. Other synthetic pozzolanic materials can include, without limitation, fumed silica, calcined clays, crushed glass (e.g., recycled glass), or materials that contain crushed glass, slags, and the like.

Natural pozzolanic materials that can be included in the blend of cementitious materials can include natural materials of volcanic origin such as volcanic ashes, perlite and pumices. Volcanic materials are generally largely composed of volcanic glass. Other natural pozzolanic materials include deposits in which the volcanic glass has been altered to zeolites by interaction with alkaline waters. Diatomaceous earths, formed by the accumulation of siliceous diatom microskeletons, and other types of finely ground naturally siliceous materials can also be utilized.

When included, the blend of cementitious materials can generally incorporate about 80% or less by weight of one or more pozzolanic materials, for instance from about 20% by weight to about 80% by weight, from about 25% by weight to about 75% by weight, or from about 30% by weight to about 60% by weight.

The blend of cementitious materials can include additional materials as are generally known in the art such as, for instance, and without limitation filler, aggregates, and other structural materials as well as various chemical admixtures that can be utilized to modify characteristics of the cementitious materials.

Aggregates can include fine aggregate, such as natural or manufactured quartz or basaltic sand, and/or course aggregate, such as limestone, granite, gneiss, basalt; heavy weight sand and gravel, e.g., hematite, magnetite or barite or light weight aggregate such as, pumice, vermiculite, or diatomaceous earth. Manufactured aggregates include polymeric beads, formed or crushed ceramic, heavy weight steel or other metal, and light weight expanded clays or shales.

Additives to the cementitious material can include structural fillers such as fibers, e.g., steel, glass, ceramic, carbon, polymeric, or natural fibers, as well as mesh, rebar, and the like. For example, polymeric fibers including polyolefins, polyamides (e.g., nylon), polyester, polymethylpentene, polyacrylonitrile, polyacrylamide, viscose, nylon, PVC, PVA, rayon, or any mixtures thereof. Reinforcing fibers may include but are not limited to various forms of cellulose fibers such as chemical, mechanical or thermal-mechanical pulps, and mineral wool. Fibrous reinforcement materials can include fibers of any suitable size and geometry.

The cementitious material can include additives such as ion exchange resins, zeolites, iron powders, titanate compounds, phosphate compounds, attapulgite clay, and so forth. The additives can be treated as desired, for instance, attapulgite clay may be heat treated (calcined) to modify the surface crystal structure and provide improved adsorptive capabilities to the additive. In one embodiment, the cementitious material can be made less permeable to water by the addition of a clay such as bentonite.

Additives such as air entraining agents, water reducers, plasticizers, water proofing and others can be incorporated in the blend of cementitious materials. Additives may include but are not limited to density modifiers, dispersing agents, silica fume, geothermal silica, fire retardants, thickeners, pigments, colorants, dispersants, foaming agents, flocculating agents, waterproofing agents, organic density modifiers, aluminum powder, kaolin, alumina trihydrate, mica, calcium carbonate, wollastonite, polymeric resin emulsions, and mixtures thereof. Additive may include organic and/or inorganic molecules, and may comprise small molecules, polymers or mixtures thereof. Additives can include an accelerator for reducing set time, a retarder for delaying set time, a superplasticizer, an air-entraining agent for freeze-thaw resistance, a corrosion inhibitor, an expansive admixture for minimizing shrinkage, a shrinkage reducing admixture, a water repelling admixture, a water reducer (including high-range water reducers), an alkali-aggregate reaction inhibitor (e.g. lithium-based salts), or a mixture thereof.

In one embodiment, the cementitious material can include a form of waste. For example, the cementitious material can include a low activity radioactive waste or a chemically hazardous waste and the cementitious material can be a waste form. According to this embodiment, a solution containing the waste, for instance a radioactive salt solution can be combined with a blend of cementitious materials and cured to form the waste material, e.g., the waste material known as saltstone. To form the low activity salt solution used in forming saltstone, a precipitation-adsorption process is first carried out to decontaminate a salt solution including multiple isotopes such as cesium-137, strontium-90, ruthenium-106, plutonium and technetium-99 (Tc-99). One suitable decontamination process is disclosed in U.S. Pat. No. 4,432,893 to Lee, et al., the contents of which are incorporated herein by reference. According to this process, the major radioactive components of the salt solution, cesium-137, strontium-90 and plutonium, are removed by contacting the radioactive waste solution simultaneously with sufficient sodium tetraphenylborate to precipitate the cesium, and with sufficient sodium titanate to adsorb the strontium and plutonium. The solids can then be separated (for example, by cross-flow filtration) from the salt solution. The resulting decontaminated salt solution includes Tc-99, which remains as the predominant long-lived radionuclide. According to one embodiment, such a decontaminated salt solution can be combined with a blend of cementitious materials to form an aqueous-based cementitious slurry, which cures via hydration reactions to produce the waste form referred to as saltstone.

According to the present disclosure, a sample of the cured cementitious material that includes the redox active transition metal indicator can be tested to determine the location of an oxidation front in the material. The oxidation front is the depth to which oxygen has been transported into the material via air or dissolved in water and has oxidized/solubilized chemical species (e.g., Tc-99 or Cr) of interest. Initially, a sample of the material can be obtained as a core or grab sample from the production/processing/disposal facility or from a sample produced in the laboratory. In general, the sample can be at a predetermined depth from a surface of the material. The sample can be tested as obtained or, in one embodiment, the sample can be crushed or ground to increase the surface area of the sample. When the sample is ground, the particulate size of the sample is not particularly critical.

In one embodiment, a bore or grab sample can be sliced into "depth discrete" wafers and each wafer tested to determine the oxidation profile, and depth to which the sample has been oxidized. In one embodiment, the sample can be obtained and (optionally) crushed to smaller size in an anaerobic atmosphere. While this is not a requirement of the testing methods, in those embodiments in which the sample is not obtained and treated in an anaerobic atmosphere, the sample should be tested as quickly as possible following initial separation from the bulk material, so as to avoid oxidation of reduced components of the test sample during sample preparation.

To determine the redox condition of the cementitious material, the sample is combined with anaerobic water and held in an anaerobic atmosphere for a period of time to promote leaching of the redox active transition metal indicator from the sample and at the same time prevent inadvertent oxidation (or reduction) of the redox indicator during the leaching process. The testing water can be de-aerated according to any suitable method. For instance, in one embodiment the water can be boiled for a period of approximately 15 minutes and cooled in a sealed container. In one embodiment, the anaerobic water can be ASTM Type 1 water and meet the requirements for deionized water as described in ASTM 1193. For instance, the water can have a resistivity at 25° C. of less than about 18 MΩ-cm and can have a conductivity at 25° C. of less than about 0.056 µs/cm.

The mixture can be agitated to encourage contact between the solid and liquid. For instance, the mixture can be stirred, rotated, tumbled, etc. The contact/leaching/extraction time is variable. Results have been obtained for samples leached 18 hr and 28 days. Longer and shorter leaching times as well as times between 18 hr and 28 days can be viable and reasonable and depend on the properties of the waste form. For instance, the mixture including the solid sample and the anaerobic water can be held in an anaerobic atmosphere for a period of time of about 10 minutes or more, for instance from about 15 minutes to about 30 days, or even longer, to allow leaching of materials from the solid to the leachate. The preferred time for the leaching process can vary depending upon the size of the sample, the particulate size of the sample, etc. as is known in the art.

Following a period of time, the leachate can be examined to determine the presence or quantity of the redox indicator. The leachate should be properly treated so as to prevent any false results. For example, if the redox active transition metal indicator is soluble in the reduced state, care should be taken to prevent oxidation of the leachate prior to the examination, which could cause the indicator to precipitate out of solution and lead to a false result. Under the anaerobic conditions of the test, in those situations in which the cementitious sample is in a reduced state, a redox active indicator that is insoluble in the reduced state can also be in a preserved or reduced state, and there can be little or no indicator present in the leachate. When the cementitious sample is oxidized, the redox indicator can be oxidized and soluble, and the leachate can contain a nominal amount of the indicator. In one embodiment, the indicator can have a detectable color depending upon the oxidation state, and the leachate can be examined visually to determine the redox condition of the sample, In one embodiment, the leachate can be examined via spectroscopy to determine the redox condition of the sample.

The leachate from a reduced sample can have a characteristic absorption profile as compared to the leachate from an oxidized sample.

The method of examination is not intended to be limited to spectroscopy, however. For example, the leachate can be examined by ICP-OES ICP-MS, liquid scintillation counting or other methods understood and used by one of ordinary skill in the art. This disclosure does not limit the method of analysis used to identify the redox indicator's oxidation state.

One or more samples can be taken from a bulk cementitious material to determine the oxidation condition of the material at various depths. For instance, multiple samples can be taken at various depths as determined from an oxidized surface of the material to determine the location of an oxidation front within the sample. The location of an oxidation front can be determined, for instance by incremental sample testing of a bore taken through the depth of the material, and the rate of oxidation of the material can be determined. In one embodiment, a single sample can be taken at the farthest depth from an exposed surface of the cementitious material to determine if the entire sample is oxidized.

The present disclosure may be better understood with reference to the example, set forth below.

Example 1

A low level waste simulant was formed including the components of the table, below:

| Compound | Molarity (moles/liter) | Molecular Mass (grams/mole) | Amount/Liter (grams) |
|---|---|---|---|
| $Al(NO_3)\cdot 9H_2O$ | 0.110 | 375.129 | 41.23 |
| 50 wt. % NaOH | 1.551 | 39.998 | 124.07 |
| $Na_2SO_4$ | 0.059 | 142.042 | 8.32 |
| $Na_2CO_3$ | 0.148 | 105.990 | 15.64 |
| $Na_2NO_3$ | 2.116 | 84.995 | 179.86 |
| $NaNO_2$ | 0.336 | 68.996 | 23.20 |

Samples were prepared in batches ranging from 150 to 1500 grams. Batches were prepared by first adding the simulant solution to a beaker. The simulant solution was stirred by a mechanical mixer containing a 6-blade paddle impeller at approximately 250 rpm. Some of the samples were spiked with a chromium redox active transition metal in its fully oxidized form: Cr(VI). The spike chemical was sodium chromate ($Na_2CrO_4$). The spike was added at nominal concentrations of 20 ppm, 500 ppm, 1000 ppm, 5000 ppm, 10,000 ppm, and 20,000 ppm based on sample mass. The spike material was added to the simulant solution before addition of the remaining components of the cementitious blend and allowed to stir for a minimum of 5 minutes or longer until the spike material appeared dissolved. Samples were also formed with no spike materials. Saltstone samples without spikes inherently contain the redox active elements Fe and S.

The remaining components of the cementitious blend were combined in a bag and then added to the simulant as the simulant stirred. Components of the cementitious blend included 45% blast furnace slag (BFS) 45% thermally beneficiated Class F fly ash, and 10% ordinary Portland cement by mass at a nominal 0.6 water to solids ratio. Samples containing no blast furnace slag were also formed and included 45% fly ash and 55% cement as components where blast furnace slag was substituted by cement.

The resultant grout slurry was mixed for about 3 minutes at an increased rpm that produced a vortex in the grout without entraining air. The grout was subsequently poured into 1½"× 3¹¹⁄₁₆" (referred to as 1×4) polypropylene sample cylinders at a fill volume of about 80% to 100% and capped. The samples were cured (stored) in a humid chamber at ambient temperature and 65-70% relative humidity, until the samples were used for testing.

For testing, cylinders were removed from the plastic vials and wafers were sliced from the cylinders starting from the top surface that was exposed to air. A Techcut4™ saw with a low concentration diamond blade and jig was used to cut the wafers. The nominal blade speed while cutting samples was 200 rpm. The samples were cut dry (no water or other lubrication), and plastic forceps were used for handling cut pieces to reduce cross-contamination. ASTM type I water (ASTM D1193) and tissue paper were used to clean the saw blade between cuts to avoid cross-contamination. Care was taken to minimize the sample handling time and thereby the time the demolded samples were exposed to air (oxygen). Minimal oxidation during sample preparation was later confirmed by the chromium leaching results for non-oxidized bulk material (far from the exposed surface), which were 1000 times less than the results for the top surface.

The thinnest wafer that could be cut with the TECHCUT4™ saw was 1.5 mm. Samples representing layers for depths less than 1.5 mm were achieved with a small stainless steel spatula by scraping the surface of the grout cylinders into a disposable polystyrene weighing dish. A caliper was used to measure sample dimensions. The smallest division for the caliper used to measure samples was ¹⁄₁₀ mm. Measurements less than the smallest division were estimated based on relative position between readings. Sample heights and thicknesses were always measured in two directions (i.e., 90° apart or opposite).

Wafer samples were ground using a mortar and pestle. The size-reduced sample was placed into a leaching vial and weighed. Each vial contained a unique mass of material which depended on the thickness of the layer sampled. The amount of leachate also varied because each vial was completely filled. The vial was completely filled with the de-aerated ASTM water.

ASTM Type 1 water (ASTM 1193) was utilized as the leaching solution. The pH of the water was 6.94. The water was de-aerated by boiling in an open stainless steel container for 15 minutes. The water was subsequently cooled to room temperature in a sealed container that was placed in an ice bath before contacting the crushed samples. Less than 5 hours elapsed between boiling the water and filling the leaching vials. Vials were always filled so no air pocket remained after capping. An analytical balance was used to determine the sample mass and leachate volume (assuming 1 g/mL). The mortar and pestle was cleaned with ASTM water and tissue paper between subsamples.

Leaching was performed using a modified Toxicity Characteristic Leaching Procedure (TCLP) approach (EPA Manual SW-846 Method 1311). Multiple vials were individually wrapped and placed inside a large mouth bottle that was tumbled end-over-end for 20 hours. The tumbler rotated at 30 rpm.

After tumbling, the leachate was extracted and filtered using a 0.45 micron membrane. The concentration of Cr, the redox active transition metal indicator, was measured using an Inductively Coupled Plasma (ICP) optical emission spectrometer, Varian 730-ES. Other species were analyzed to benchmark (baseline) other properties of the material and support interpretation of the transition metal redox active indicator results. Concentrations of $Al^{3+}$, $Ca^{2+}$, $K^+$, and $Na^+$ were analyzed via ICP and concentrations of $Cl^-$, $NO_2^-$, $PO_4^-$, $F^-$, $NO_3^-$, $SO_4^-$ and $C_2O_4^{2-}$ were analyzed using Ion Chromatography (IC).

The filtrate was diluted up to 1000 times in some cases to accommodate the detection ranges and equipment sensitivity for constituents. The pH and conductivity of the filtrates were also determined using an IQ Scientific pH meter and a Thermo Scientific Orion 4 Star conductivity meter. ASTM Type I/II water was used to clean the probes between samples. Leachate analyses were run in duplicate. Values were averaged and used to calculate the fraction leached (percent leached) for a sample set cured for 35 to 37 days. Percent of each species leached was calculated using the following equation:

$$\% \text{ leached} = 100 \times (m_{i\text{-}leached}/m_{i\text{-}total})$$

where:

$m_{i\text{-}leached}$=mass of species i leached (mg).
$m_{i\text{-}total}$=mass of species i in the waste form (mg).

The fraction of the transition metal indicator leached or the percent leached (fraction leached×100) from each crushed wafer was selected as the parameter for contaminant leaching results and for demonstrating applicability of this method in determining the effective oxidation front. The top surfaces of the samples were exposed to air in the sample vials and the redox active transition metal indicator was expected to be oxidized to soluble species near the surface and reduced as insoluble species at some depth below the exposed surface. Contaminants that are not redox sensitive such as $NO_3^-$ were expected to have about the same fraction leached regardless of location of the sample relative to the top surface.

Results for the transition metal redox indication, Cr, and several non-redox sensitive species, e.g., Na and $NO_3^-$ were plotted as a function of sample interval. Nitrate results were used to compare the effect of microstructure (microencapsulation) on the leaching results for species that are not chemically bound in the waste form. Nitrate is, at best, only weakly bound in slag and no slag matrices. The microstructures, (i.e., pore size distribution and tortuosity) are different for these two waste forms, and therefore, the nitrate extraction rate is expected to be slightly different.

Figure 1B:
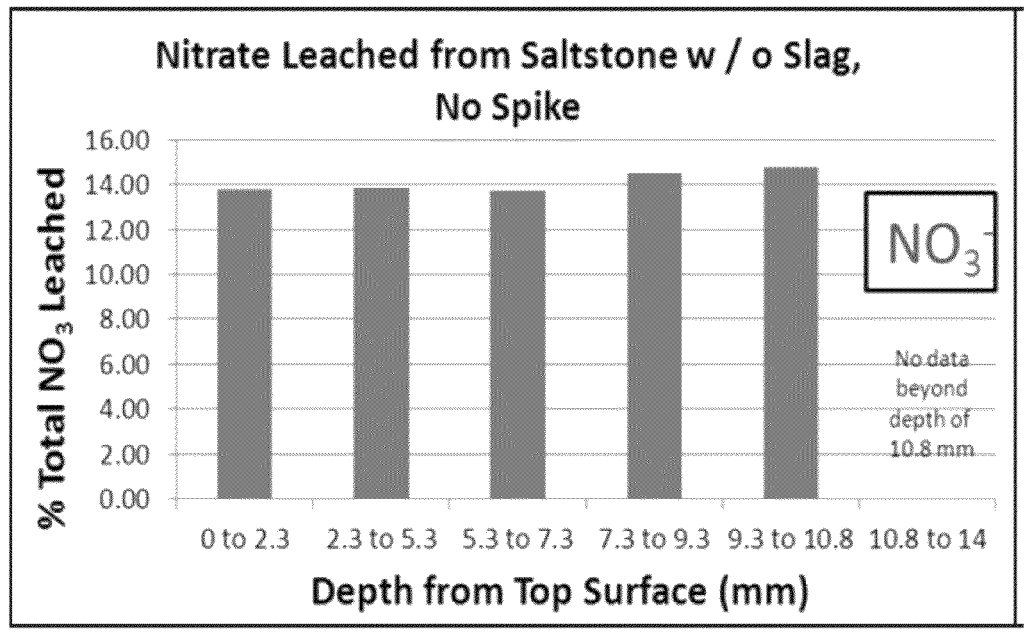

The chromium fraction leached from the no-slag waste form ranged between 0.05 and 0.08 and appeared to be independent of the sample depth-interval. (FIG. 1A). The depth interval pattern is consistent with that for $NO_3^-$ leached from the no-slag waste form (FIG. 1B). A comparison of chromium and $NO_3^-$ leached from the chromium-spiked sample suggests that chromium is slightly better bound in the no-slag sample (cement-fly ash matrix) than $NO_3^-$ (about 2.25× better).

Figure 2A:
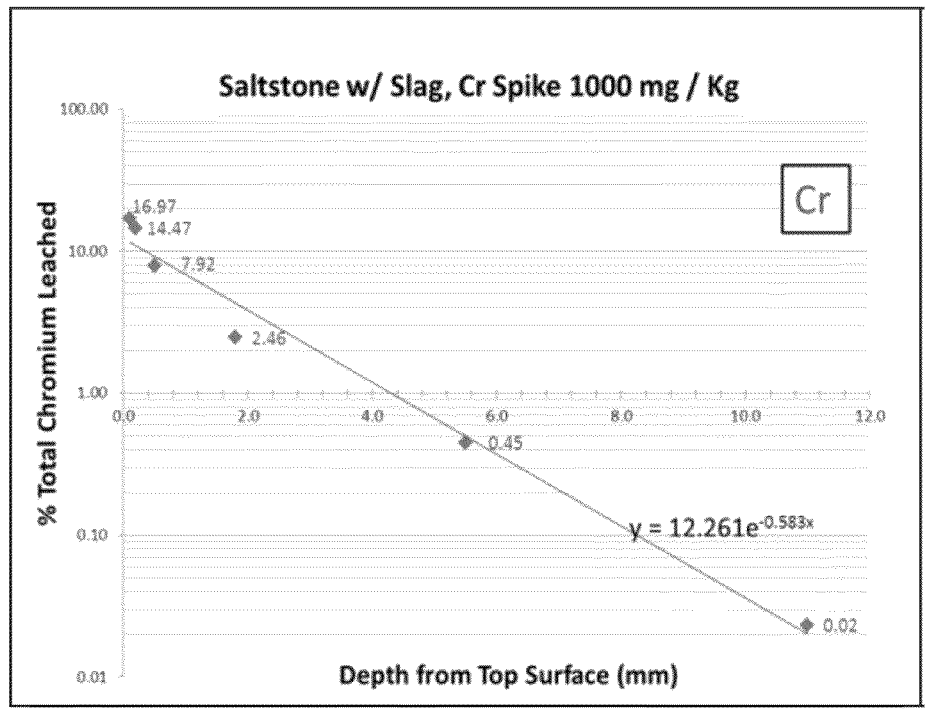
FIG. 2 illustrates the fractions of chromate (FIG. 2A, FIG. 2B) leached from cementitious saltstone samples that include ground granulated blast furnace slag.
Figure 2B:
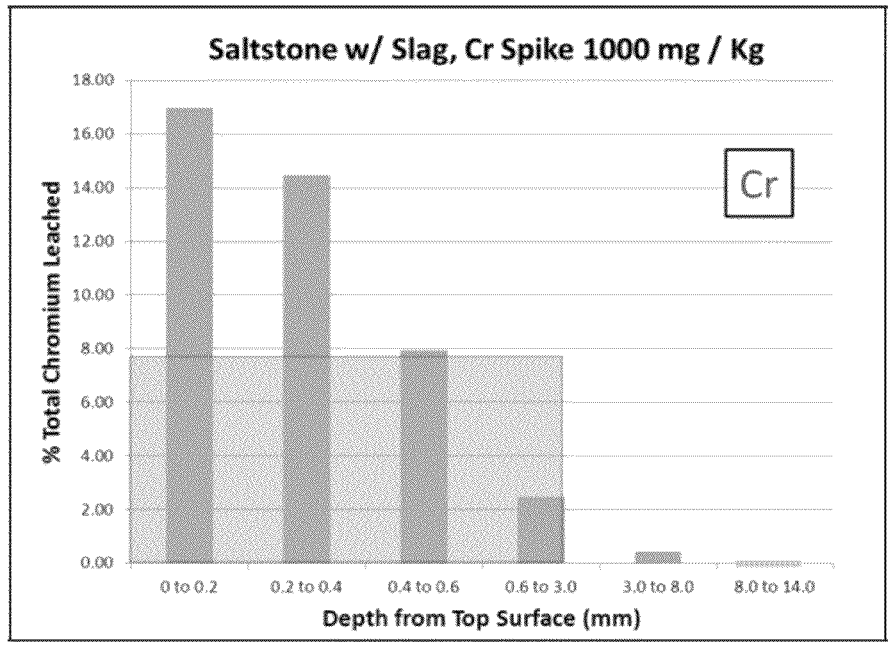

The chromium fraction leached from the slag saltstone sample ranges from about 0.17 from the exposed surface to 0.0002 from a layer 8.0 to 14.0 mm below the exposed surface. This is a difference of about 1000× as illustrated in the semi log plot provided in FIG. 2A. FIG. 2B illustrates fractions of chromium leached as a function of distance from the top surface.

The chromium fractions leached from the top 7 mm of the slag saltstone sample indicated that chromium was more oxidized in samples collected nearer to the surface. Therefore, the effective Cr oxidation front was approximately 8 mm below the surface for the sample. These results were interpreted to infer that chromium was chemically stabilized in the slag saltstone matrix to the extent that the fraction leached was 1000 times less than that of $NO_3^-$, which was only very slightly bound in the matrix.

The leaching results indicated that post-curing conditions related to the exposed surface affected the chromium leachability from the slag saltstone samples. Even though the amount of oxygen in the air above the sample was somewhat limited it appears have contained enough oxygen to oxidize a portion of the chromium at the surface layer to a depth of about 8 mm. The resulting oxidized chromium formed chromate ions and was soluble. The amount of chromium leached from the various layers cut from the no slag saltstone was fairly uniform regardless of the distance from the top surface.

Example 2

Field samples were prepared similar to those described in Example 1. However, samples were filled to the top to mitigate oxygen exposure to the sample until placement in the field. Samples were stored in a humid box with their caps closed for a period of generally 1 to 3 weeks until they were transferred to the specified field location. A location was selected to provide exposure to environmental conditions while providing some shelter from rain and direct sunlight, in an attempt to simulate disposal unit performance. Two installments of samples were placed in the field. The samples were uncapped and placed into a closed chest along with an open container of water. The chest was secured with a zip-tie to restrict access. The samples cured in the area for about 4 months before they were analyzed.

Temperature and relative humidity were monitored from inside the sample chamber every hour using an EM50 series datalogger by Decagon using an EHT Temp/RH digital sensor. Relative humidity ranged from 26.3-99.6% and temperature ranged from 14.3-41.4° C. (57.7-106.5° F.) fluctuating daily corresponding to daily weather conditions.

The simulated salt solution and blend of cementitious materials were formed as described in Example 1. The blend of cementitious materials included blast furnace slag as previously described. The simulated salt solution was spiked with chromium in an amount of 1000 mg/kg, 500 mg/kg, or 20 mg/kg, based on the sample size.

The chromium-spiked 1000 and 20 mg/kg samples were retrieved for testing following total curing times of 118 and 105 days, respectively. The 500 mg/kg sample was retrieved following a total curing time of 111 days.

Macroscopic differences were evident among the samples spiked with 1000, 500, and 20 mg/kg chromium. The surface of 1000 mg/kg chromium sample was a medium tan color and the top ~5 mm was light tan. The exterior surfaces of the 500 and 20 mg/kg chromium spiked samples were dark to medium gray. The top ~5 mm of each of these the samples was light gray. The sample containers were completely filled and the color change was apparent before removing the samples from the containers.

The cured saltstone samples were removed from the 1×4 inch containers and sectioned perpendicular to the long axis. A sample holder was fabricated to enable sectioning of slices as thin as 0.1 to 0.2 mm. The samples were crushed and leached in de-aerated, deionized ASTM Type I water for 18 hr.±2 hr. Leaching was performed using a modified TCLP approach (EPA Method 1311).

After leaching, the leachates were filtered and analyzed for the transition metal redox indicator, Cr. Concentrations and pH of other species were analyzed to benchmark (baseline) other properties of the material and support interpretation of the transition metal redox active indicator results. Other cations and anions of interest included $Al^{3+}$, $Ca^{2+}$, Fe, $K^+$, $Na^+$, $NO_2^-$, $NO_3^-$, and $SO_4^{2-}$.

Leachate analyses were run in duplicate. Values were averaged and used to calculate the fraction leached (percent leached). The percent of the selected ions leached from the crushed sub-samples was determined as described in Example 1.

Figure 3:
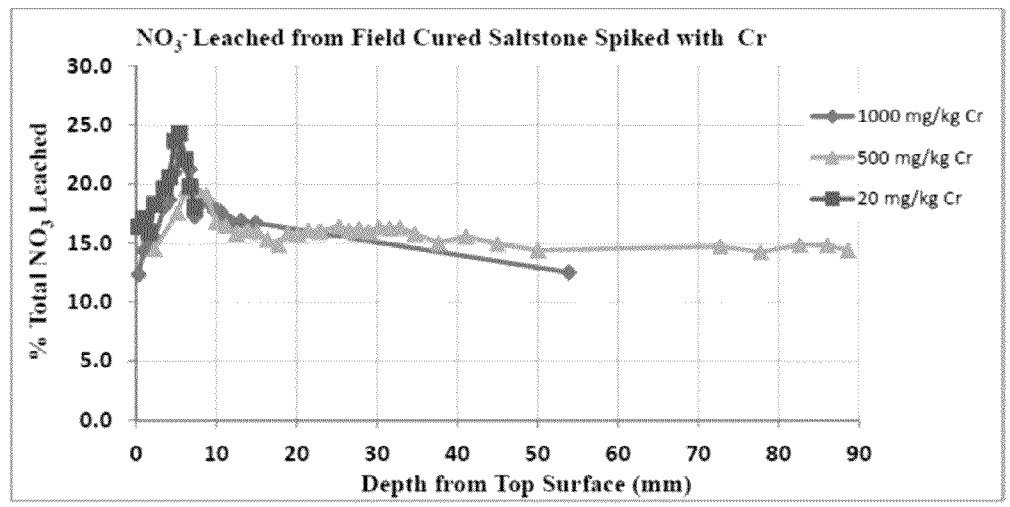
FIG. 3 illustrates the fraction of nitrate leached as a function of depth of the sample from field-cured saltstone samples that include a chromium indicator.
Figure 4:
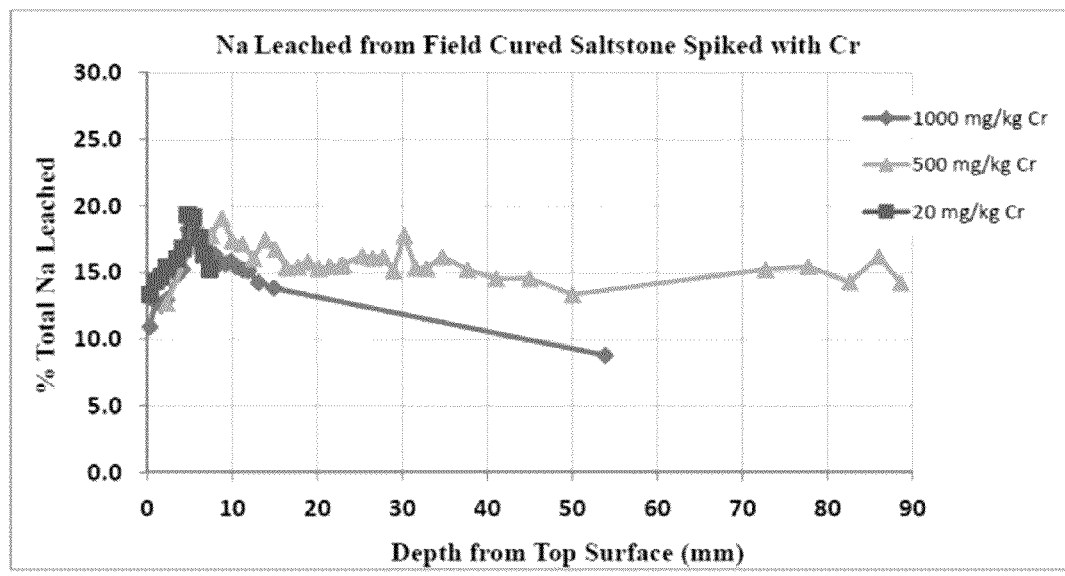
FIG. 4 illustrates the fraction of sodium leached as a function of depth of the sample from field-cured saltstone samples that include a chromium indicator.
Figure 5:
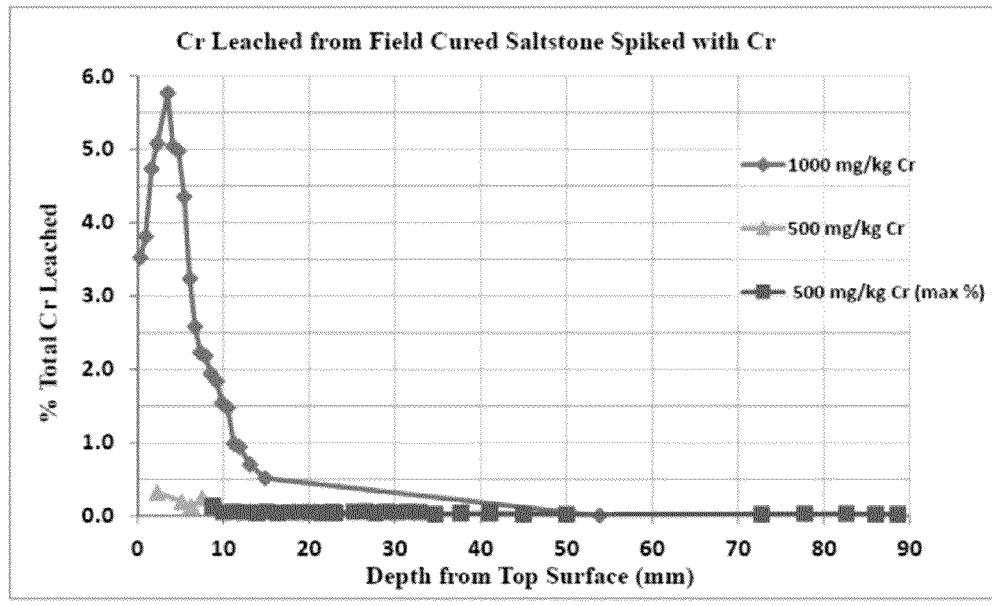
FIG. 5 illustrates the fraction of a chromium indicator leached as a function of depth of the sample from field-cured saltstone samples.

The fractions leached as a function of sample distance from the exposed top surface are plotted for $NO_3^-$, sodium, and chromium in FIG. 3, FIG. 4, and FIG. 5, respectively. The three samples evaluated were assumed to be identical except for the amount of chromium added as a spike. The fractions of $NO_3^-$ leached as a function of distance from the top of the sample were similar for all three samples. The percentages of sodium leached as a function of distance from the top of the samples were also similar to those for nitrate although the sodium profiles as a function of depth from the top are not as sharp and well defined as those for $NO_3^-$. For both of these species, about 10% of the total amount in the first layer was extracted in the 18 hour test. The percentages extracted increase for subsequent layers to 20 to 25% depending on the sample's depth of 5 to 6 mm from the top surface. The percentages extracted then decrease to about 15% at about 12 mm from the top surface and remain at 15% throughout the remainder of the sample. About 9 percent of the total sodium was extracted from a subsample cut from the middle of the sample spiked with 1000 mg/kg chromium.

The leaching behavior for chromium, the transition metal redox sensitive indicator, as a function of distance from the top exposed surface also exhibited a spike in the percentage leached for subsamples collected about 3 to 5 mm from the top surface followed by a sharp decrease in the percentages of chromium extracted between 5 and 10 to 15 mm from the top surface. However, the percentages of chromium leached as a function of depth from all three chromium field cured samples (chromium spikes of 1000, 500, and 20 mg/kg) were significantly lower than the percentages of $NO_3^-$ and Na leached from the corresponding subsamples. Thus demonstrating the effectiveness of Cr as a transmission metal redox indicator to identify the oxidation front in this type of material.

Figure 6:
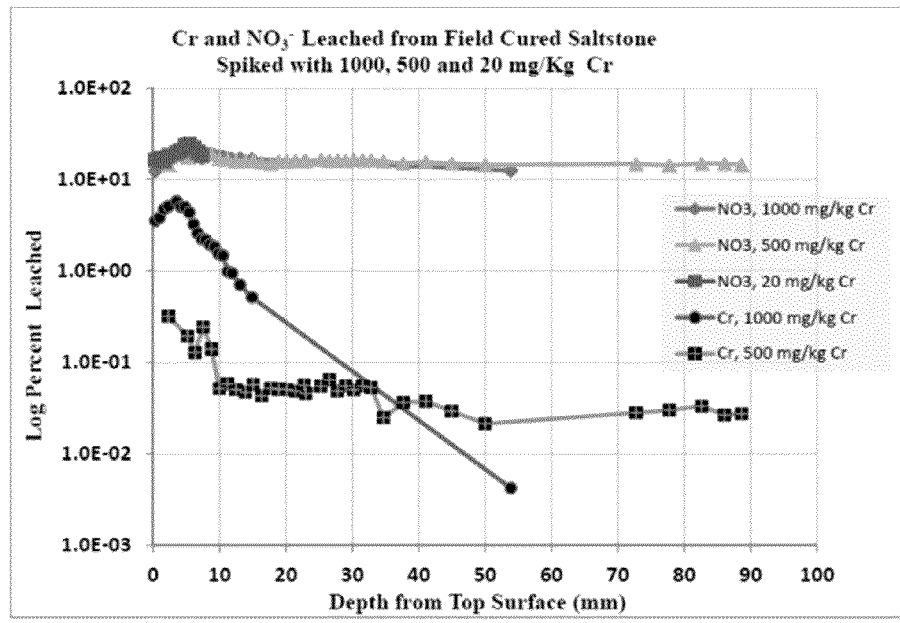
FIG. 6 compares the fraction of nitrate and chromium leached as a function of depth of the sample from various field-cured saltstone samples.

The maximum percentage of chromium leached from the sample spiked with 1000 mg/kg chromium was 5.8% compared to 22.4, 19.4, and 24.3%, the maximum percentages of $NO_3^-$ leached from samples spiked with 1000, 500, and 20 mg/kg chromium, respectively (FIG. 5 and FIG. 6). In addition between 10 and 20 mm from the exposed top surface, the amount of chromium detected in the leachates from samples spiked with 500 mg/kg were below the limit of detection, 0.01 mg/L. All of the leachates from the sample spiked with 20 mg/kg chromium were below the chromium detection level of 0.01 mg/L. Consequently the percentages reported and plotted are over estimates of the actual values.

The bulk material was considered to be samples collected from 15 to 90 mm below the exposed surface. About 15% of the total nitrate was extracted from crushed (powdered) field cured samples from material collected more than about 15 mm below the top surface. In comparison, only about 0.05% of the chromium added to the samples was extracted from subsamples more than about 15 mm below the top surface for samples spiked with 500 and 1000 mg/kg chromium. This difference in magnitude is illustrated in the semi-log graph shown in FIG. 6. Leachate results for the sample spiked with 20 mg/kg chromium were all below the detection level; <0.01 mg/L; consequently meaningful percentages extracted could not be calculated.

These results suggest a depth of oxidation as reflected in the increased percentage of chromium leached between 2 and 10 mm from the surface. Based on the observed leaching profiles (observed spikes between 3 and 10 mm from the surface) for chromium and $NO_3^-$, the top portion of the samples appears to not be representative of the bulk (non-oxidized portion) of the samples cured for between 111 and 118 days under field conditions. The fraction of chromium leached from the top 20 to 30 mm appears to be a function of the chromium concentration in the sample. The percentages of chromium leached from samples spiked with 1000 mg/kg chromium were about 10 times higher than the percentages of chromium leached from samples spiked with 500 mg/kg chromium over this depth. (Comparisons were not possible for samples prepared with 20 mg/kg chromium because the amount of chromium leached was below the detection level of 0.01 mg/L and less than values resulted in false percentages that overstate the true values.)

Figure 7:
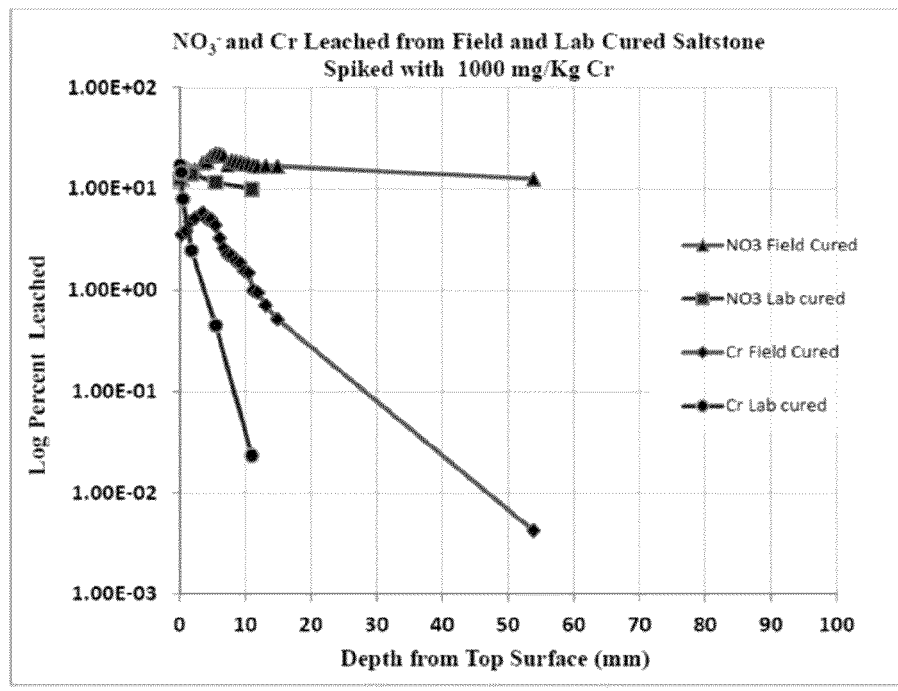
FIG. 7 compares the fraction of nitrates and chromium leached as a function of depth from the sample from lab-cured and field-cured saltstone samples.

A comparison of the $NO_3^-$ and chromium leached from a laboratory cured sample (37 days) and from a field cured sample (118 days) is provided in FIG. 7. Both samples were spiked with 1000 mg/kg chromium and contain identical proportions of ingredients. The spike pattern for the percentage leached as a function of distance from the exposed surface for sub-samples cut near the top of the cylinders is characteristic of $NO_3^-$ and chromium in the field cured sample. This pattern is present but less well defined for $NO_3^-$ in the laboratory cured sample. The pattern was not observed for chromium in the laboratory cured sample (see FIG. 7). The different exposure times, 37 days (lab cured sample) versus 118 days (field cured sample), may account for some or all of this difference.

The leaching experiments performed in this study were assumed to approximate but not necessarily resulted in equilibrium partitioning of any chemical species between the liquid and solid phases. Therefore, distribution ratios, $R_d$, were reported rather than equilibrium distribution coefficients. Distribution ratios are calculated from the same formula as distribution coefficients, $K_d$'s as shown the following equation:

$$R_d = [\text{Concentration of species in the solid phase}](\text{mg/kg})/[\text{Concentration of species in the liquid phase}] (\text{mg/L})$$

Figure 8:
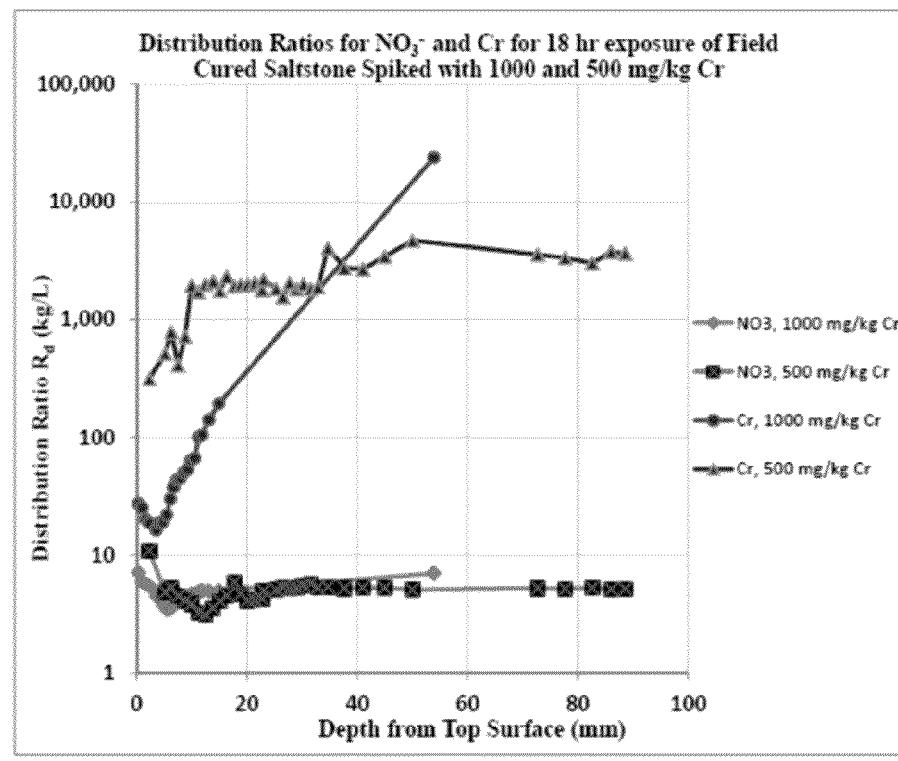
FIG. 8 compares the nitrate and chromium distribution ratio for an 18 hour anaerobic extraction as described herein.

The relationship between percentage leached and distribution ratio is provided in the equation below. Percentages of $NO_3^-$ and chromium extracted from field cured saltstone were converted into distribution ratios (non-equilibrium) to illustrate the difference between physical stabilization and chemical stabilization in the saltstone matrix (see FIG. 8).

$$R_d = [100 - \% \text{ leached into the liquid phase}]/[\% \text{ leached into the liquid phase}]$$

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for determining the location of an oxidation front in a cured cementitious material, the method comprising:

obtaining a sample from a cured cementitious material, the sample being obtained at a depth from a surface of the cured cementitious material, the cementitious material including a redox active transition metal indicator that exhibits variable solubility in a solvent depending upon the oxidation state of the redox active transition metal indicator;

combining the sample with de-aerated water to form a mixture, the mixture including a liquid portion that includes the de-aerated water and a solid portion;

maintaining the mixture under anaerobic conditions for a period of time to form a leachate;

examining the leachate following the period of time to determine the presence or quantity of the redox active transition metal indicator in the leachate, the presence or quantity of the redox active transition metal indicator in the leachate being indicative of the redox condition of the sample of the cured cementitious material and the location of the oxidation front in the cured cementitious material.

2. The method according to claim 1, wherein the redox active transition metal indicator is cobalt, copper, iron, manganese, nickel, niobium, rhenium, ruthenium, tantalum, technetium, titanium, or vanadium.

3. The method according to claim 1, wherein the redox active transition metal indicator exhibits variable solubility in an aqueous solvent.

4. The method according to claim 1, wherein the cementitious material includes ground granulated blast furnace slag.

5. The method according to claim 1, wherein the cementitious material comprises a filler or an aggregate.

6. The method according to claim 1, wherein the cementitious material comprises a rheology modifying additive.

7. The method according to claim 1, wherein the cementitious material comprises a low activity waste or chemically hazardous waste.

8. The method according to claim 1, further comprising agitating the sample during the step of maintaining the mixture under anaerobic conditions.

9. The method according to claim 1, wherein the leachate is examined by use of one or more of spectroscopy, inductively coupled plasma optical emission spectrometry, inductively coupled plasma mass spectrometry, or liquid scintillation counting.

10. The method according to claim 1, the method comprising repeating the method with one or more additional samples obtained from the cementitious material, wherein the one or more additional samples are obtained from different depths of the cementitious material as determined from a surface of the cementitious material.

11. The method of claim 1, wherein the method is also utilized to determine the rate of oxidation and location of the oxidation front of the cementitious material.

12. The method according to claim 1, wherein the redox active transition metal indicator is soluble in an oxidized state and is insoluble in a reduced state.

13. The method according to claim 12, wherein the redox active transition metal indicator is chromium.

14. The method according to claim 1, wherein the cementitious material includes a calcium silicate cement.

15. The method according to claim 14, wherein the calcium silicate cement comprises Portland cement.

16. The method according to claim 1, wherein the cementitious material includes a natural or synthetic silica or alumino-silica pozzalanic material.

17. The method according to claim 16, wherein the pozzolanic material comprises fly ash.

18. The method according to claim 1, further comprising treating the sample to increase the surface area of the sample prior to the step of combining the sample with the de-aerated water.

19. The method according to claim 18, wherein the sample is treated under anaerobic conditions.

* * * * *